United States Patent [19]

Eldridge

[11] 4,207,870

[45] Jun. 17, 1980

[54] BLOOD SAMPLING ASSEMBLY HAVING POROUS VENT MEANS VEIN ENTRY INDICATOR

[75] Inventor: William N. Eldridge, Rutherford, N.J.

[73] Assignee: Becton, Dickinson and Company, East Rutherford, N.J.

[21] Appl. No.: 915,670

[22] Filed: Jun. 15, 1978

[51] Int. Cl.² ............................................. A61B 5/14
[52] U.S. Cl. .................................. 128/766; 128/764; 128/218 NV; 128/274; 137/854; 137/197
[58] Field of Search ................ 128/2 F, DIG. 5, 274, 128/218 NV, 214.4, 762–766; 73/425.4 P; 137/854, 197, 199

[56] References Cited

U.S. PATENT DOCUMENTS

| | | | |
|---|---|---|---|
| 2,913,000 | 11/1959 | Roberts | 137/854 |
| 3,817,240 | 6/1974 | Ayres | 128/2 F |
| 3,859,998 | 1/1975 | Thomas | 128/214.4 |
| 3,864,979 | 2/1975 | Ayres | 73/425.4 P |
| 4,016,879 | 4/1977 | Mellor | 128/214.4 |
| 4,046,144 | 9/1977 | McFarlane | 128/214.4 |

FOREIGN PATENT DOCUMENTS

| | | | |
|---|---|---|---|
| 826926 | 1/1952 | Fed. Rep. of Germany | 137/854 |
| 2726011 | 12/1977 | Fed. Rep. of Germany | 128/214.4 |

Primary Examiner—Kyle L. Howell
Attorney, Agent, or Firm—Kane, Dalsimer, Kane, Sullivan and Kurucz

[57] ABSTRACT

A blood sampling assembly is provided which has a cannula designed for intravenous penetration, a mechanism for applying negative pressure to the cannula, a chamber located between the cannula and the source of negative pressure, a one-way valve positioned within the chamber, and a venting member within the chamber which allows the venting of air as blood enters the chamber, but does not allow the passage of blood. A person drawing blood is enabled to visually determine when a needle is properly inside a vein through transparent walls of the chamber. Spillage of blood is avoided with the present assembly by the resistance of the one-way valve to flow distally from the intravenous cannula.

10 Claims, 4 Drawing Figures

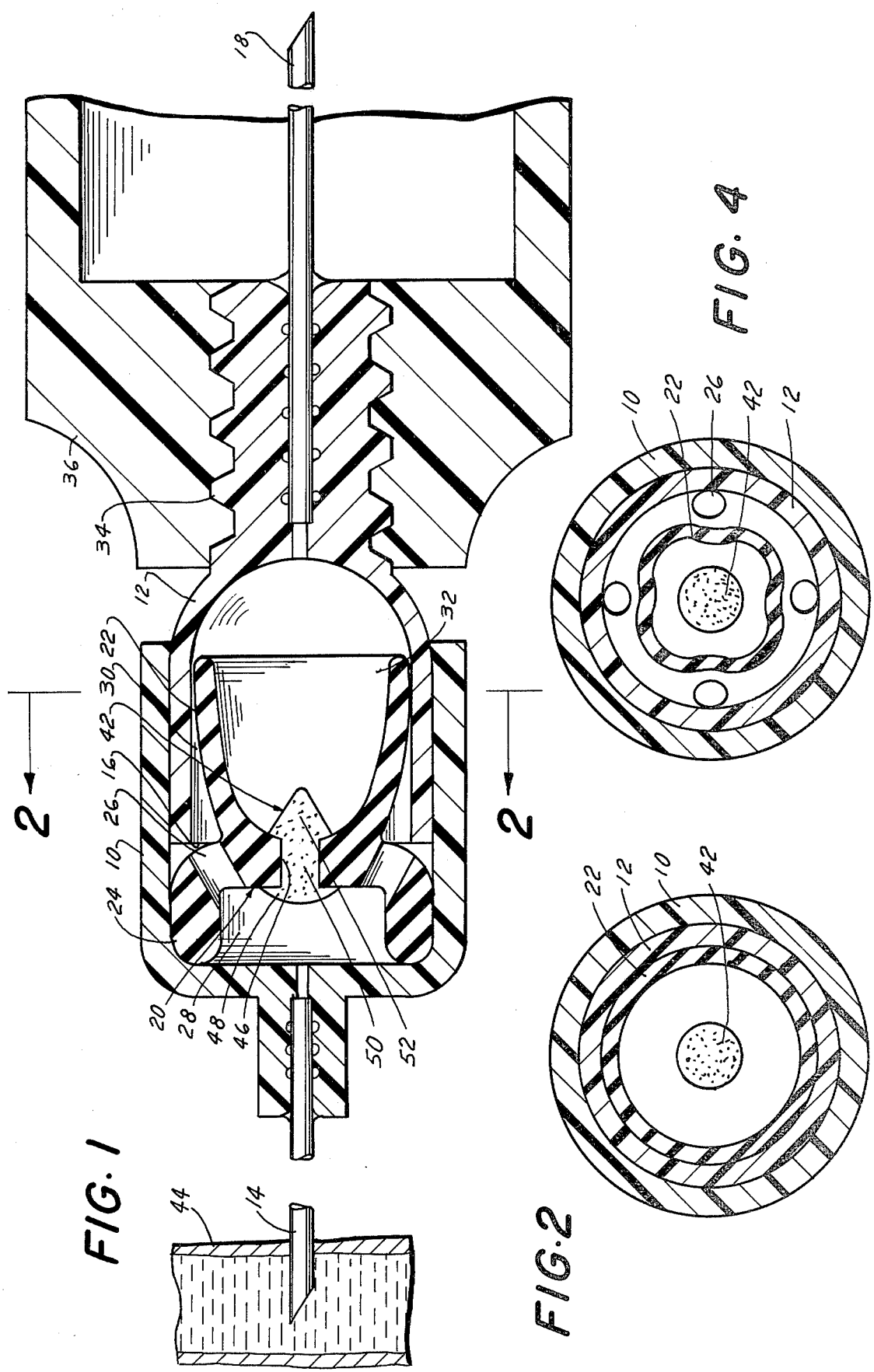

4,207,870

BLOOD SAMPLING ASSEMBLY HAVING POROUS VENT MEANS VEIN ENTRY INDICATOR

BACKGROUND OF THE INVENTION

The field of the invention concerns blood sampling devices which provide a visual indication of venipuncture.

Blood sampling needles currently in commercial use do not allow the phlebotomist (person drawing blood) to know when the needle is properly inside the vein. This is especially a problem with small or tough veins.

A method often used involves watching for the presence of blood dripping from the needle point which is designed for penetration of the stopper of an evacuated blood collection container. This is messy, and is considered traumatic to the patient or donor.

Another method involves actually trying to draw a blood sample with an evacuated collection tube. If this fails, the phlebotomist still does not know for sure if the vein is improperly punctured or if the vacuum in the collection tube might be dissipated.

The utilization of a porous filter which permits the flow of air more readily than blood is known to the art. Commonly assigned U.S. Pat. Nos. 3,864,979, and 4,016,879 are examples of blood sampling devices having such filters. These filters have been advantageously applied for enabling a nurse or physician to readily determine whether the selected vein has been pierced and entered.

SUMMARY OF THE INVENTION

It is an object of the present invention to provide a blood sampling needle having a means for reliably indicating venipuncture.

It is another object of the invention to provide a needle assembly which allows multiple sampling, that is, the taking of a number of samples of blood using the same one venipuncture.

Still another object of the invention is to provide an assembly having all the above mentioned advantages which is simple and economical in manufacture.

With the above objectives in mind, a blood sampling device is provided having a cannula designed for intravenous penetration; a source of negative pressure to be applied to the cannula; a chamber located between the cannula and source of negative pressure, the chamber being at least partially transparent or translucent; a one-way valve positioned within the chamber, the valve permitting flow towards the rear of the device when the negative pressure is applied; and venting means within the chamber which allow the passage of air as blood enters the chamber, but does not allow the passage of blood for at least a reasonable amount of time.

The one-way valve and the venting means cooperate to provide significant advantages for the patient and phlebotomist. The valve is constructed to allow the flow of blood therethrough only when the source of negative pressure has been applied. When the intravenous cannula is first injected, blood will flow through the cannula and into the chamber. Flow will then cease as neither the valve nor the venting means are designed to allow the flow of blood under the pressures ordinarily associated with a patient's vein, even under tourniquet pressure. Air is displaced as blood enters the chamber, and exits by way of the vent. The chamber which has walls which are at least partially transparent or translucent enables the phlebotomist to visually determine whether the vein is properly punctured.

After venipuncture, the source of negative pressure is applied. This source may be an evacuated collection container having a rubber stopper. The stopper is pierced by a second cannula which is located on the sampling device downstream from the one-way valve. Blood may be quickly collected in this manner.

As opposed to the concurrently filed application Ser. No. 915,669, filed June 15, 1978, the valve itself is not intended to selectively allow the passage of air under low pressure and the flow of blood when the source of negative pressure is applied. Fluid takes the path of least resistance, and the least resistance to gaseous flow is provided by the vent means.

The vent means is easily manufactured for the reliable venting of air under tourniquet pressure, and is utilized instead of the valve in permitting the flow of gas.

The invention as described herein provides numerous advantages, including: (1) the avoidance of messy conditions and patient trauma due to spillage; (2) greater safety, since no blood with possible contamination would come in contact with the phlebotomist, (3) the reliable indication of venipuncture as air vents from inside the device to allow blood to enter, and the blood being visible therein due to the translucent or transparent design, and (4) the prevention of undesired blood flow or leakage upon penetration of a vein or between the taking of multiple samples.

Other body fluids may also be sampled with the invention.

BRIEF DESCRIPTION OF THE DRAWINGS

FIG. 1 is a sectional elevation view of the blood sampling assembly wherein the vent means is a porous plug inserted within the valve member;

FIG. 2 is a cross-sectional view of the invention taken along line 2—2 of FIG. 1;

FIG. 4 is a cross-sectional view taken along line 4—4 of FIG. 3;

DETAILED DESCRIPTION OF THE INVENTION

Figure 3:
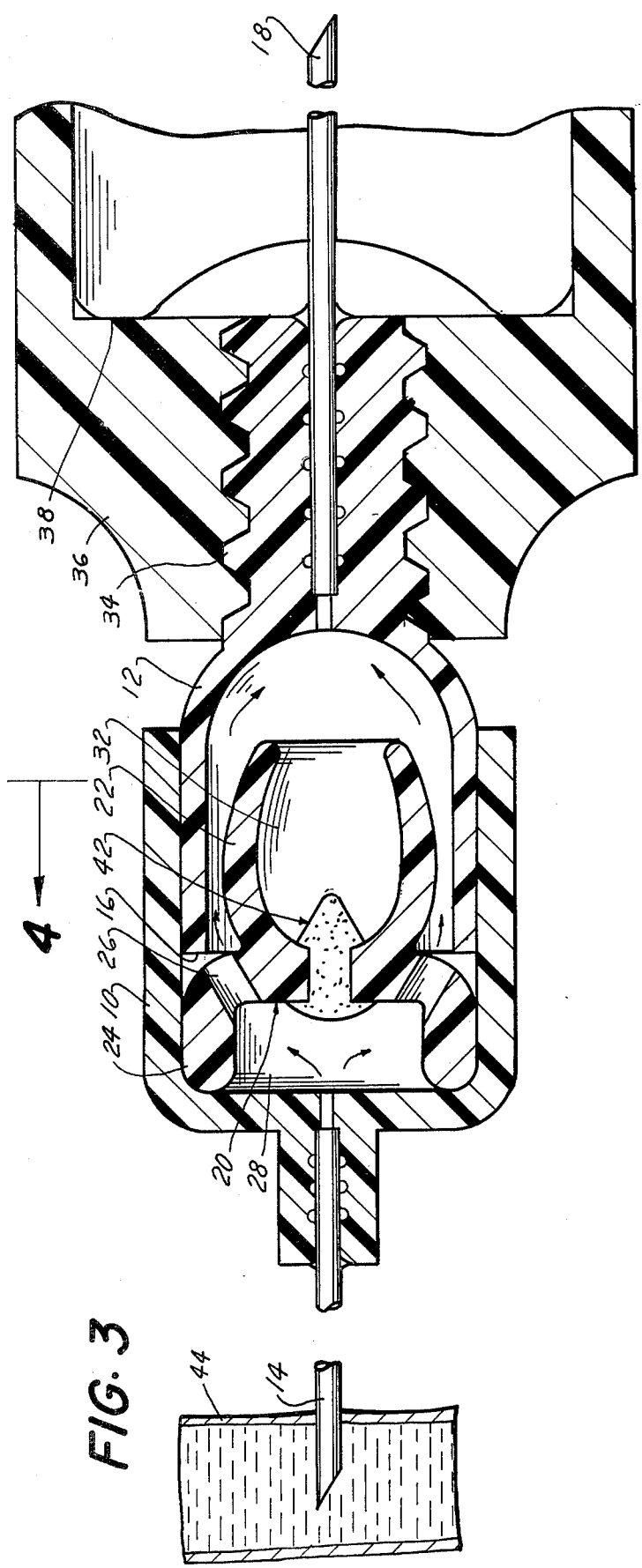
FIG. 3 is a sectional elevation view of the assembly after an evacuated collection container has been applied.

FIG. 1 is a sectional elevation view of the invention as it is used to puncture a vein. Two needle hubs 10 and 12 are provided, the first hub 10 having an intravenous cannula 14 attached by epoxy or any other suitable means. The distally located hub 12 is attached to the first by conventional means so as to provide a shoulder 16 within the device. A second cannula 18, designed for penetration of the stopper of an evacuated container, is secured to this hub 12.

A cup-shaped valve member 20 is located within the device, its upper portion 24 being positioned between the inner walls of hub 10 and shoulder 16. This prevents displacement of the valve member. Passages 26 are provided in the valve member for allowing fluid to pass in the direction of resilient skirt 22. Open spaces or chambers 28 and 30 are present between, respectively, the inner wall of hub 10 and valve member 20, and the inner wall of hub 12 and the outer surface of skirt 22.

The distal end of hub 12, which includes cannula 18, is adapted for securement to a collection tube holder, and threads 34 are provided for this purpose. The pointed end of needle 18 is adapted for puncturing the stopper 38 of an evacuated tube, such as a Vacutainer tube, manufactured by Becton, Dickinson and Company of Rutherford, N.J.

The valve member 20 is also provided with a porous plug 42. The plug is gas permeable, but preferably is to a degree liquid impermeable and serves to inhibit or deter the passage of blood therethrough so as to prevent spillage from the distal end of the device. The plug 42 may be fabricated from a wide variety of materials having the desired properties of porosity. Porous polyethylenes (also known as open cell polyethylene foam), porous polypropylene, porous polyfluorocarbons, and similar polymeric resin materials are examples of suitable materials. An open pore structure with pore sizes of about 5-50 microns is contemplated, most preferably in the neighborhood of about 10 microns. The plug may be fabricated by conventional methods such as molding or casting, and is designed so as to be insertable within a hole 46 provided within the valve member 20. The plug has a mushroom shaped upper portion 48, a stem 50, and an enlarged lower portion 52 which may taper towards the distal end for ease of insertion. This typical configuration provides for retention of the plug in the valve means under both positive and negative pressure. The stem fits within the hole 46, and the upper and lower portions 48 and 52 prevent movement in either direction. Blood cannot leak through the hole 46 as the plug is frictionally sealed therein.

In most contemplated procedures, a tourniquet is applied to the patient raising the blood pressure at the puncture sight to about 60-65 cm of water. The cannula 14 is injected within a vein 44, and blood enters the cannula. As the blood flows through the cannula 14 and into the chambers 28 and 30, air is displaced through the venting means 42 to the atmosphere via cannula 18. This allows the blood to fill the chambers, and the phlebotomist can easily determine that a vein has been properly punctured by observing the blood through the transparent walls of the hubs 10 and 12. Leakage cannot occur as neither the porous plug (or vents) nor valve skirt 22 allows the transfer of blood under the pressures usually associated with this procedure. FIG. 2 illustrates the sealing relationship of the valve skirt 22 with the walls of the hub under tourniquet pressure.

Once it has been determined that a vein has indeed been punctured, an evacuated tube having a stopper 38 may be inserted within the distal end of holder 36 such that the stopper is penetrated by the distal end of cannula 18. This creates the necessary negative pressure to collapse the valve skirt 22 as shown in FIGS. 3 and 4, and allows the flow of blood into the chamber 32, cannula 18, and ultimately the collection tube (not shown).

When the pressures are equalized between the puncture sight and the distal end of cannula 18, the valve skirt returns to the position shown in FIGS. 1 and 2. This prevents the further flow of blood, and allows the exchange of collection tubes without spillage if it is desired to take another blood sample. The one-way valve also protects against backflow into the patient should a pressure reverse occur.

Those skilled in the art will appreciate that other embodiments may be devised which fall within the spirit and scope of the invention. The scope of the invention should accordingly be determined by reference to the appended claims.

What is claimed is:

1. A multiple blood sampling assembly adapted to be coupled with an evacuated container to obtain blood samples from a patient, comprising:
   a housing having a forward end and a rear end and having a chamber therein, the chamber having walls which are at least partially translucent;
   a first cannula mounted to a forward end of the housing and in fluid communication with the chamber;
   a second cannula mounted to the rear end of the housing and in fluid communication with the chamber;
   a cup chaped one-way valve positioned within the chamber and having a resilient skirt which sealingly bears against the walls of the chamber when blood flows under tourniquet pressure from said first cannula; and
   venting means in the form of a porous material within said chamber, said venting means positioned within said chamber such that blood may flow under tourniquet pressure from the first cannula into the chamber only up to the point where the one-way valve is located as gas is displaced through the venting means, the venting means also positioned such that gas is displaced from a portion of the chamber on a side of the valve towards the first cannula, through the venting means, and to the atmosphere via the second cannula.

2. A multiple blood sampling assembly adapted to be coupled with an evacuated container to obtain blood samples from a patient, which provides a visual indication of venipuncture without the spillage of blood, comprising:
   a housing having a forward end and a rear end and having a chamber therein, the chamber having walls which are at least partially translucent;
   a cannula mounted to the forward end of the housing and in fluid communication with the chamber;
   a one-way valve within the chamber, said valve permitting flow distally from the patient only when a source of negative pressure is applied; and
   a porous plug inserted within said one-way valve, said plug allowing the flow of gas therethrough but substantially preventing the flow of blood, the valve and plug positioned within said chamber such that blood may flow from the cannula into the chamber up to the point where the one-way valve is located as gas is displaced through the porous plug.

3. An assembly as described in claim 2 wherein the one-way valve is a cup-shaped valve having a resilient skirt which forms a sealing relation with the walls of the chamber.

4. An assembly as described in claim 3 wherein the one-way valve is provided with a hole near the closed portion of the cup, and the plug comprises upper and lower portions having larger dimensions than the hole and a stem portion connecting the upper and lower portions, said stem portion having smaller dimensions than said upper and lower portions, the stem portion of the plug being positioned within the hole in the valve, and the upper and lower portions preventing displacement of the plug.

5. An assembly as described in claim 2 wherein a second cannula is attached to the rear end of the housing, said second cannula being in fluid communication with the chamber.

6. An assembly as described in claim 5 further including in combination an evacuated container in fluid communication with the second cannula.

7. An assembly as described in claim 5 wherein the housing includes means for attaching a holder for an evacuated container.

8. An assembly as described in claim 7 wherein the means for attaching a holder comprises screw threads.

9. An assembly as described in claim 7 further comprising in combination a holder for an evacuated container attached to the housing.

10. An assembly as described in claim 9 further comprising in combination an evacuated container within the holder.

* * * * *

UNITED STATES PATENT AND TRADEMARK OFFICE
CERTIFICATE OF CORRECTION

PATENT NO. : 4,207,870
DATED : June 17, 1980
INVENTOR(S) : William N. Eldridge

It is certified that error appears in the above—identified patent and that said Letters Patent is hereby corrected as shown below:

Claim 1, column 4, line 12, "chaped" should be --shaped--.

Signed and Sealed this

Sixteenth Day of September 1980

[SEAL]

Attest:

SIDNEY A. DIAMOND

*Attesting Officer*   *Commissioner of Patents and Trademarks*